Figure 1:
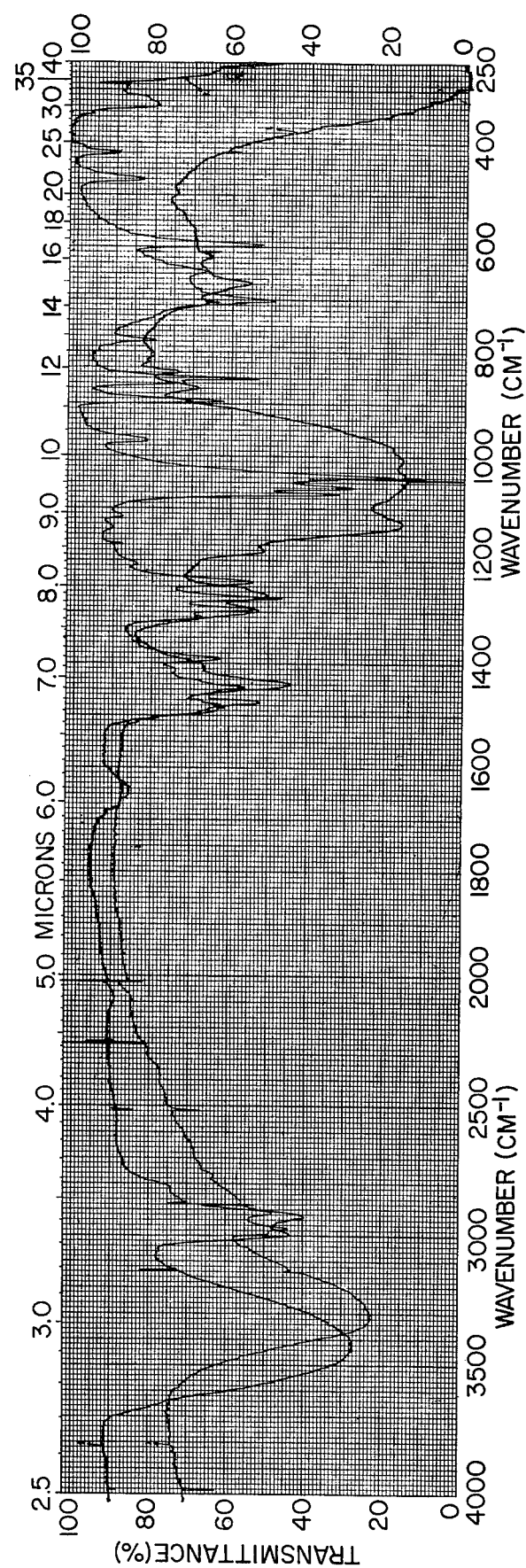

United States Patent [19]

Ravey

[11] 4,394,306
[45] Jul. 19, 1983

[54] BROMINE CONTAINING FIRE RETARDANT COMPOSITIONS OF MATTER

[75] Inventor: Manny Ravey, Haifa, Israel

[73] Assignee: IMI (Tami) Institute for Research & Development Ltd., Haifa, Israel

[21] Appl. No.: 256,476

[22] Filed: Apr. 22, 1981

[30] Foreign Application Priority Data

May 23, 1980 [IL] Israel .......................................... 60149

[51] Int. Cl.$^3$ ............................................... C09K 3/28
[52] U.S. Cl. ................................ 252/609; 106/18.14; 106/18.24; 428/921; 521/158
[58] Field of Search ........................ 252/607, 608, 609; 521/158; 428/921; 568/599; 106/18.14, 18.24

[56] References Cited

U.S. PATENT DOCUMENTS 3,100,135  8/1963  Sexsmith ........................... 568/599 X
4,155,900  5/1979  Walters ............................ 252/609 X
4,301,058  11/1981 Neukirchen ....................... 252/609 X

FOREIGN PATENT DOCUMENTS 1230007  12/1966  Fed. Rep. of Germany ....... 568/599
768778   2/1957   United Kingdom ................ 568/599
1361134  7/1974   United Kingdom ................ 568/599

Primary Examiner—Leland A. Sebastian
Attorney, Agent, or Firm—Schwartz, Jeffery, Schwaab, Mack, Blumenthal & Koch

[57] ABSTRACT

The present invention relates to novel fire retardant compositions, based on the compounds 2-bromomethyl-2-hydroxy-methylpropane-1,3-diol, 2,2-bis(bromomethyl)propane-1,3-diol, 2-bromomethyl-2-hydroxymethyl-1,3-dibromopropane, and mixtures thereof, the compositions having a general formula $(BrCH_2)_m C[CH_2O(CH_2O)_xH]_{4-m}$ wherein m is between 1.6 to 2.3 and x is between 0.75 to 1.10. These compositions are characterized by their particular infra-red spectra.

The novel fire retardant compositions are produced by the reaction of formaldehyde or its polymeric forms with the above compounds, followed by the removal of water from the reaction system.

The fire retardant compositions according to the present invention are suitable as active or additive fire retardant ingredients for various polymeric materials, such as polyurethane, polyester or epoxide resins.

15 Claims, 1 Drawing Figure

BROMINE CONTAINING FIRE RETARDANT COMPOSITIONS OF MATTER

The present invention relates to novel fire retardant compositions. More particularly the invention relates to novel compositions of matter comprising bromine-containing compounds, to be used as fire retardants for various polymeric materials.

Bromine containing compounds are commonly used for the fire retardation of numerous polymeric materials. Such fire retardants can be applied in two forms, as active or as additives. An active fire retardant is one that interacts chemically with the substrate, so that it becomes permanently incorporated into the polymer structure. An additive retardant does not involve any chemical interaction between the fire retardant and the polymeric substrate, the additive being dissolved or dispersed in the polymer matrix and therefore it can be lost from the substrate in various ways. Typical examples of the latter are materials with appreciable vapor pressure which may vaporize out, incompatible materials which bleed and soluble materials which can be leached out. Therefore it is clear that where the chemical and physical properties of the polymer permit, an active fire retardant is preferable.

The effectiveness of a fire retardant is closely related to its structure, which not only determines the chemistry or mechanism of the inhibition of combustion, but also influences the overall properties of the product. Dibromoneopentyl glycol (2,2-bis-bromomethylpropane-1,3-diol) hereinafter referred to as DBNPG, is a well known active fire retardant. DBNPG finds application for the fire retardation of a variety of condensation polymers where one of the raw materials contains an hydroxy group, or alternatively, a group capable of chemically reacting with the hydroxy groups of the DBNPG. Examples of such systems, but not limited to them are: polyesters, polyurethanes, epoxides and polycarbonates. DBNPG has found particular application in unsaturated polyester resins and rigid polyurethane foams. The structure of DBNPG confers to it a relatively high thermal stability which is markedly higher than many other aliphatic bromo-compounds, a fact which also contributes to its outstanding properties as a fire retardant.

One of the main disadvantages of DBNPG in its application to the fire retardation of polyurethanes is its limited solubility and slow dissolution rate in many of the raw materials commonly used for the preparation of polyurethane foams. DBNPG is a crystalline solid and in order to achieve an homogeneous product, the DBNPG must be dissolved in one or more of the reagents prior to their interaction. Dispersion in the form of a very fine powder, although theoretically possible, in practice may cause complications since the presence of solids often leads to blockage of the lines and nozzles of equipment used in the manufacture of polyurethane products. DBNPG reacts with the isocyanate component of the polyurethane formulations, so that it is preferable to introduce it dissolved in the polyol component. However most of the commercially available polyols, including polyesters, polyethers and castor oil-based materials, exhibit relatively low solubilization capacities for DBNPG. This limits the amount of this material which can be incorporated into the final product and accordingly will affect the flame retardation property. This is particularly so when the fire retardant is added to only one of the components as in the case for polyurethanes. It is often desired to incorporate fire retardants to the extent of about twenty percent, or even more, into the final product. It is clear therefore that its limited solubility gives DBNPG a disadvantage for many polyurethane compositions.

One approach to overcome the above mentioned deficiencies is to form a derivative of DBNPG which is miscible with, or very soluble in, a wide variety of polyols. Such a derivative should not contain groups which detract from the properties of the basic structure, that is its chemical reactivity in the incorporated form, nor should the bromine content be significantly reduced by derivatization. In an attempt to meet these objections the Dow Chemical Company developed a liquid flame retardant which is a DBNPG-based adipic acid ester. This material (known under the Trademark XNS-50044) is proposed for use in polyurethane formulations, with which it is claimed to be readily compatible. It is prepared by esterifying DBNPG with adipic acid (two moles of DBNPG and one mole of adipic acid) thus obtaining a hydroxyl terminated ester (D. P. Miller, Journal of Cellular Plastics, July/August 1979, pages 211-219) in the form of a viscous liquid. However it suffers from the disadvantages of being of relatively high cost. A further disadvantage of the adipate is its tendency to form a very viscous mass due to some polyester formation. Thus the present state of the art, indicates the existence of a long felt need for a suitable DBNPG-based soluble fire retardant form. It is an object of the present invention to provide new compositions of matter based on brominated pentaerythritol, which are useful as fire retardants. It is another object of the present invention to provide new compositions of matter based on 2-bromomethyl-2-hydroxymethylpropane-1,3-diol, 2,2-bis(bromomethyl)propane-1,3-diol, 2-bromomethyl-2-hydroxymethyl-1,3-dibromopropane, and mixtures thereof which are obtained by a simple chemical reaction using inexpensive reagents. Thus the invention consists in novel compositions of matter of formula $(BrCH_2)_mC[CH_2O(CH_2O)_xH]_{4-m}$ wherein $m=1.6$ to 2.3 and $x=0.75$ to 1.10, obtained by the hydroxymethylation (as hereafter defined) of 2-bromomethyl-2-hydroxymethylpropane-1,3-diol, 2,2-bis(bromomethyl)propane-1,3-diol, 2-bromomethyl-2-hydroxymethyl-1,3-dibromopropane, and mixtures thereof containing an average of 1.7 to 2.5 hydroxyl groups per molecule, with formaldehyde or its polymeric forms, said compositions of matter being useful as active or additive fire retardants for polymeric materials. The term hydroxymethylation in the context of the present application, means the substitution of the hydrogen atom of the alcoholic hydroxyl groups by —CH$_2$OH groups, which is represented as follows for the case of a sample alcohol:

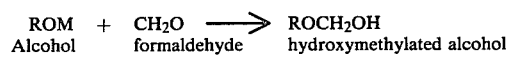

ROM + CH$_2$O ⟶ ROCH$_2$OH
Alcohol    formaldehyde    hydroxymethylated alcohol

Since the hydroxymethylated alcohol contains an alcoholic hydroxyl group, it can react further with additional formaldehyde to form polyoxymethylene hemiformals:

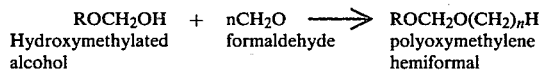

Hydroxymethylated alcohol + nCH$_2$O → ROCH$_2$O(CH$_2$)$_n$H polyoxymethylene hemiformal Even when equivalent quantities of reagents are used, some polyoxymethylene hemiformal formation may take place, leaving in solution a proportional amount of the original alcohol unreacted. Furthermore, in cases such as the present one, in which the starting material comprises a compound having a plurality of hydroxy groups per molecule, the hydroxymethylated product may contain some mono-hemiformal, the compound which results from the reaction of only one of the hydroxyl groups.

The compounds which constitute one of the starting reagents according to the present invention, consist of dibromoneopentyl glycol 2-bromomethyl-2-hydroxymethylpropane-1,3-diol, 2-bromomethyl-2-hydroxymethyl-1,3-dibromopropane, or mixtures thereof. As known, commercial DBNPG is obtained by the bromination of pentaerythritols. Depending on the method of operation, the product may be a relatively pure DBNPG or mixtures of 2-bromomethyl-2-hydroxymethylpropane-1,3-diol, 2,2-bis(bromomethyl)propane-1,3-diol, and 2-bromomethyl-2-hydroxymethyl-1,3-dibromopropane, wherein an average of 1.7 to 2.5 of the hydroxyls per molecule have been replaced by bromine. This represents a mixture of 2-bromomethyl-2-hydroxymethylpropane-1,3-diol, 2,2-bis(bromomethyl)propane-1,3-diol and 2-bromomethyl-2-hydroxymethyl-1,3-dibromopropane whose concentration ranges vary from 5% 2-bromomethyl-2-hydroxymethylpropane-1,3-diol, 80% 2,2-bis(bromomethyl)propane-1,3-diol and 15% 2-bromomethyl-2-hydroxymethyl -1,3-dibromopane to 15% 2-bromomethyl-2-hydroxymethylpropane-1,3-diol, 80% 2,2-bis(bromomethyl)propane-1,3-diol, and 5% 2-bromomethyl-2-hydroxymethyl-1,3-dibromopropane. The residual hydroxyl groups of this mixture of compounds can also be readily hydroxymethylated. Therefore instead of utilizing pure DBNPG, the latter can be successfully replaced by the less expensive mixtures.

The novel compositions of matter are characterized by their bromine content which lies between 40% and 55% by wt. and preferably between 48% and 53% when applied to pure DBNPG. Such products are generally liquids and readily miscible with a large variety of those polyols which are used in the manufacture of polyurethanes. The product obtained by the use of equivalent quantities of reagents, or even a slight excess of formaldehyde is predominatly the dihemiformal of dibromoneopentyl glycol having a bromine content of 49-50% (calculated for the dihemiformal 49.7%). The dihemiformal retains two hydroxyl groups which react with the isocyanate component of the polyurethane as readily as do those of DBNPG itself.

Since the hydroxymethylated DBNPG according to the present invention is intended mainly for use as a fire retardant component, it is desirable to maintain a bromine content as high as possible in the product, thus minimizing the polyoxymethylene content, since the latter is a source of fuel for combustion. According to another embodiment of the present invention, it is possible to increase the bromine content deliberately by underhydroxymethylating DBNPG i.e. using less than the equivalent amount of formaldehyde, to the extent that the product will meet the intended requirements, e.g. solubility in the matrix. The product obtained will consist substantially of mixtures of the monohemiformal and dihemiformal, which have been found to be very useful as fire retardants.

Formaldehyde constitutes the second starting reagent according to the present invention. It can be used either in its aqueous form as commercially available, containing about 36-38% by weight formaldehyde, or in its polymeric forms such as trioxymethylene (CH$_2$O)$_3$ or paraformaldehyde (CH$_2$O)$_n$·H$_2$O.

Reactions between carbonyl groups and alcohols, to which family of reactions the subject of this application belongs, have been studied extensively and the conclusion reached is that the addition products can be isolated only in rare cases. This is clearly stated in "The Chemistry of the Ether Linkage" (E. Schmitz and I. Eichorn, Interscience N.Y., S. Patai, Editor, 1967, page 309) and in other sources. The inventor of the present invention found this to be true in regard to the interaction of DBNPG with several carbonyl compounds. In the experiments which he performed it was found that the reaction products of acetaldehyde and propionaldehyde, respectively with DBNPG are very unstable, containing large amounts of solid unreacted DBNPG. It was surprisingly found in according with the present invention that formaldehyde, or its polymeric forms, reacts easily with DBNPG, the hemiformal obtained being quite stable. In the following Table 1 are presented some data on stability tests carried out on the reaction products of DBNPG and formaldehyde, acetaldehyde and propionaldehyde. Reaction products of these aldehydes were kept in open beakers for several days and were weighed periodically. The weight loss as percent of the respective aldehyde was calculated.

TABLE 1

| Period (days) | Weight loss (percentage). | | |
|---|---|---|---|
| | Formaldehyde | Acetaldehyde | Propionaldehyde |
| 1 | −1.7* | 54 | 71 |
| 4 | −2.5* | 84 | 96 |
| 11 | 5.2 | completely solid | completely solid |

*gain in weight, as percent of initial weight, probably due to absorption of atmospheric moisture.

From the above results it is clear that the acetaldehyde and propionaldehyde adducts with DBNPG are very unstable in comparison to the formaldehyde derivative. Furthermore the infra-red spectra of the reaction products show that with formaldehyde no carbonyl absorption band exists which indicates the absence of free aldehyde, while with the other aldehydes, strong carbonyl absorptions at 1735 cm$^{-1}$ were found indicating the presence of free aldehydes in both cases. The latter reactions are therefore incomplete. Any free aldehyde present after the reaction with DBNPG will be lost rapidly to the atmosphere with the formation of solid DBNPG.

The products obtained according to the present invention were also investigated by their infra-red spectra. The infra-red spectra of these products as well as of the starting DBNPG are given in FIG. 1. It appears that the products possess a very broad and strong absorption band within the range of 950-1150 cm$^{-1}$, with maxima at 1130, 1040-1050 and 1010 cm$^{-1}$ and two weak bands at 840 and 870 cm$^{-1}$.

The method of manufacture of hydroxymethylated products according to the present invention is very simple and does not require any complicated equipment. The 2-bromomethyl-2-hydroxymethylpropane-1,3-diol, 2,2-bis(bromomethyl)propane-1,3-diol, 2-bromomethyl-2-hydroxymethyl-1,3-dibromopropane, or mixture thereof is dissolved in formalin by heating to above approximately 40° C. and stirring until a clear solution is obtained. This is followed by removal of the water, preferably under vacuum, at this or higher temperatures.

As shown in the art it is sometimes preferable to use a mixture of fire retardants in some applications. Thus for example, compounds containing halogen are often synergistic in respect to fire retardation when used in combination with phosphorus and antimony containing compounds. Therefore, it may be desirable to use the compositions claimed by this invention along with additional fire retardants such as O,O-diethyl-N,N-bis(2-hydroxyethyl) aminomethylphosphonate sold by the Stauffer Chemical Company under the name "Fyrol 6".

Although the claimed compositions are admirably suited as active fire retardant ingredients to be incorporated into condensation type polymers and in particular polyurethanes, they can also be useful for application where the additive type of material is preferred. Their application in this area will of course depend on compatibility with the other components in the system.

While particular embodiments of this invention have been described, it will be evident to those skilled in the art that the present invention may be embodied in other specific forms without departing from the essential characteristics thereof. The present embodiments and the Examples presented below are, therefore, to be considered in all respects as illustrative and not restrictive, the scope of the invention being indicated by the appended claims rather than by the foregoing description and all changes which come within the meaning and range of equivalency of the claims are therefore intended to be embraced therein.

The invention will be hereafter described by the following Examples without being limited thereto. All the amounts and concentrations are expressed in weight, unless otherwise stated.

EXAMPLE 1

An amount of 2,500 parts dibromoneopentyl glycol (DBNPG) and 1980 parts of formalin solution (35–38%) were placed in a five liter flask. The mixture was stirred and heated to 70° C. until it became homogeneous and clear. Vacuum was applied to the clear solution, initially at 100 mm Hg and finally when the distillation of water ceased, at 20 mm Hg. The product, 3092 parts (calculated for dihemiformal, 3072 parts), had a bromine content of 48.7% (calculated value for the dihemiformal, 49.7%), had a hydroxy number of 350 (calculated value for the dihemformal, 348) and a Brookfield viscosity of 10300 cp at 24° C. The infra-red spectrum of the product is given in FIG. 1 (Spectrum A) versus the starting DBNPG reagent (Spectrum B).

EXAMPLE 2

10.4 Parts DBNPG and 7.6 parts formalin (35–38%) were warmed to 50° C. A clear solution formed after a few minutes. The solution was heated to 70° C. and held at this temperature for 20 minutes and then a vacuum of one millimeter was applied for two hours at this temperature. The clear pale colored viscous liquid which was obtained had a bromine content of 50.7% (calculated for dihemiformal 49.7%).

EXAMPLE 3

13 parts DBNPG and 3 parts paraformaldehyde were mixed and heated to 80° C. The mixture liquified to give a cloudy viscous liquid whose infrared spectrum was comparable to that of FIG. 1. Alternatively, part of the paraformaldehyde can be replaced with a stoichiometrically equivalent amount of formalin so as to have a more easily mixed starting mixture. In such cases the water is removed as described in Examples 1 or 2.

EXAMPLE 4

26.2 Parts DBNPG and 14.1 parts formalin solution (35–38%) were heated for one hour at 60° and then a water aspirator vacuum was applied for thirty minutes at this temperature. The resulting 31 parts of viscous liquid was equivalent in composition to an equimolar mixture of the di- and monohemiformals of DBNPG containing 52.1% bromine.

EXAMPLE 5

26.2 Parts DBNPG and 17 parts formalin solution (35–38%) were heated for 45 minutes at 50°, the temperature raised to 60° and a water aspirator vacuum applied for 20 minutes. The resulting 32 parts of viscous liquid was equivalent in composition to a 1:4 molar mixture of the mono- and dihemiformals of DBNPG containing 50.6% bromine.

EXAMPLE 6

The following mixture of 2-bromomethyl-2-hydroxymethylpropane-1,3-diol, 2,2-bis(bromomethyl)propane-1,3-diol, and 2-bromomethyl-2-hydroxymethyl-1,3-dibromopropane:

| | |
|---|---|
| $(HOCH_2)_3C(CH_2Br)$ | 5% |
| $(HOCH_2)_2C(CH_2Br)_2$ | 80% |
| $(HOCH_2) C(CH_2Br)_3$ | 15% | was hydroxymethylated using the method of Example 1 with a quantity of formalin ten percent in excess of the stoichiometrically calculated amount of one mole formaldehyde per hydroxy group. The product, when used as in Example 10 and at the same bromine concentration, exhibited a fire retardation performance very similar to that of the product of Example 10.

EXAMPLE 7

The following mixture of 2-bromomethyl-2-hydroxymethylpropane-1,3-diol, 2,2-bis(bromomethyl)propane-1,3-diol, and 2-bromomethyl-2-hydroxymethyl-1,3-dibromopropane:

| | |
|---|---|
| $(HOCH_2)_3C(CH_2Br)$ | 15% |
| $(HOCH_2)_2C(CH_2Br)_2$ | 80% |
| $(HOCH_2) C(CH_2Br)_3$ | 5% | was hydroxymethylated as in Example 6. The product, when used as in Example 9 and at the same bromine concentration, exhibited a fire retardation performance very similar to that of the product of Example 9.

EXAMPLE 8

16.1 g DBNPG hemiformal prepared according to Example 2 above were mixed with 25.8 g Polyol IN 2530 hydroxy number 350, (Polyurethane Ltd. Haifa) and to the resulting homogeneous liquid was added Freon 11,8 g, an amine catalyst b 0.5 g and finally 57.7 g MDI. The mixture was cast into a sealed mold to give a rigid foam containing 8% bromine bound into the polyurethane structure. This material exhibited the following flammability characteristics:

Limiting Oxygen Index (LOI) according to ASTM D-2863:23.0

ASTM D-1692: Self Extinguishing

Israeli Standard 755: rating I

This compares to the following values for the same foam prepared without the hemiformal of DBNPG: LOI, 19,4, ASTM D-1692, burning; Israeli Standard 755, rating I.

EXAMPLE 9

496 g. DBNPG hemiformal prepared according to Example 1 above were mixed with Fyrol 6 (a phosphorus containing reactive fire retardant manufactured by Stauffer) to give a homogeneous liquid containing 27.5% bromine and 5.5% phosphorus. 18.1 g of this solution were then mixed with 28.7 g Polyol IN, 2530.7 g Freon 11, 0.3 g catalyst and 53.2 g MDI and cast into a sealed mold to give a rigid foam containing 5% bromine and 1% phosphorus. This material had the following flammability ratings:

Limiting Oxygen Index according to ASTM D-2863:24.0

Israeli Standard 755: rating V.

EXAMPLE 10

10.2 g DBNPG hemiformal prepared according to Example 3 above were mixed with 26.2 g Polyol IN 2530,8 g Freon 11, 0.4 g catalyst, 56.1 g MDI and 7.1 g melamine phosphate (Chemicals and Fertilizers Ltd., Haifa) and the mixture cast into a sealed mold. The product contained 5% bromine, 1.5% phosphorus and had a density of 55 kg/m³.

It had the following flammability characteristics:

Limiting Oxygen Index according to ASTM D-2863:24.2

ASTM D-1692: Self extinguishing

Israeli Standard: rating V-VI.

EXAMPLE 11

16 g DBNPG hemiformal prepared according to Example 4 above were mixed with the following materials:

| | |
|---|---|
| Voranol RS-530 (a polyether polyol, Dow Chemical Co.) | 21 g |
| Atlas G-2410 (a polyether polyel, Atlas Chemical Industries) | 5.7 g |
| Silicone DC-113 (Dow Corning Corp) | 1 g |
| Trichlorfluoromethane | 13.4 g |
| Dibutyl tin dilaurate (Union Carbide Co.) | 0.1 g |
| Dimethylethanolamine (Union Carbide Co.) | 0.3 g |

This mixture was then reacted with 42 g of Nacconate 4040 in a sealed mold to give a rigid foam containing 10% bromine. This material had an LOI of 23.5 and a rating of I according to Israeli Standard 755.

EXAMPLE 12

1.8 Parts of DBNPG hemiformal prepared according to Example 1 above were mixed into 15 parts Fiberplast 555 (an unsaturated polyester resin, Fiberplast Ltd. Haifa) and the mixture cured for 5 hours at ambient followed by 5 hours at 80° C. after adding 0.15 parts MEX peroxide and 0.1 part cobalt octoate solution. The product which had a bromine content of 6 phr had a Limiting Oxygen Index of 21.7 compared to 18.8 for the same material in the absence of the DBNPG hemiformal.

I claim:

1. A composition of matter of the formula

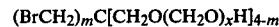

wherein m=1.6 to 2.3 and x=0.75 to 1.10, obtained by the hydroxymethylation 2-bromomethyl-2-hydroxymethyl-propane-1,3-diol, 2,2-bis(bromomethyl)propane-1,3-diol, 2-bromomethyl-2-hydroxymethyl-1,3-dibromopropane, and mixtures thereof, containing an average of 1.7 to 2.5 hydroxyl groups per molecule, with formaldehyde or its polymeric forms, said compositions of matter being useful as active or additive fire retardants for polymeric materials.

2. A composition of matter according to claim 1, wherein m=2 and x is between 1.0 to 1.1.

3. A composition of matter according to claim 1, wherein m=2 and x=0.75.

4. A composition of matter according to claim 1, wherein the infra-red spectra of said composition show a very broad and strong absorption band within the range of 950 to 1150 cm$^{-1}$ with maximum at 1130 cm$^{-1}$, 1040 to 1050 cm$^{-1}$ and 1010 cm$^{-1}$, along with two weak bands at 840 cm$^{-1}$ and 870 cm$^{-1}$.

5. A method for the manufacture of compositions of matter having the formula (BrCH$_2$)$_m$C[CH$_2$(CH$_2$O)$_x$H]$_{4-m}$ wherein m=1.6 to 2.3 and x=0.75 to 1.10, which consists in the substitution of the hydrogen atom of the alcoholic hydroxyl group by —CH$_2$OH group by the reaction of equivalent amounts of aqueous solutions of formaldehyde or its polymeric forms with 2-bromomethyl-2-hydroxymethylpropane-1,3-diol, 2,2-bis(bromomethyl)propane-1,3-diol, 2-bromomethyl-2-hydroxymethyl-1,3-dibromopropane, and mixtures thereof, followed by removal of water from the reaction system.

6. A method for the manufacture of compositions according to claim 5, wherein the amount of formaldehyde is less than the equivalent, thus producing the compositions of formula (BrCH$_2$)$_m$C[CH$_2$O(CH$_2$O)$_x$H]$_{4-m}$ wherein m=2 and x=0.75.

7. The method for the manufacture of compositions according to claim 5 or 6, wherein the brominated reactant consists of a mixture of 5% 2-dibromomethyl-2-hydroxymethylpropane-1,3-diol, 80% 2:2-bis(bromomethyl)-propane-1,3-diol and 15% 2-bromomethyl-2-hydroxymethyl-1,3-dibromopropane.

8. A method for the manufacture of compositions according to claim 5 or 6, wherein the brominated reactant consists of a mixture of 15% 2-bromomethyl-2-hydroxymethylpropane-1,3-diol, 80% 2,2-bis(-bromomethyl)propane-1,3-diol and 5% 2-bromomethyl-2-hydroxymethyl-1,3-dibromopropane.

9. A method according to claim 5 or 6, wherein the reaction between formaldehyde or its polymeric forms and said composition is carried out at temperatures of above approximately 40° C.

10. A method according to claim 5, wherein water is expelled from the reaction vessel by applying vacuum.

11. Fire retardant compositions comprising compounds, according to claim 1, together with phosphorus-containing reactive fire retardant component.

12. Fire retardant compositions comprising compounds, according to claim 1, together with O,O-diethyl-N,N-bis-(2-hydroxyethyl)aminomethylphosphonate.

13. Fire retardant compositions according to claim 11 or 12, applied to a polymeric substrate consisting of polyurethane.

14. Fire retardant compositions according to claim 11 or 12, applied to a polymeric substrate consisting of polyester.

15. Fire retardant compositions according to claim 11 or 12, applied to a polymeric substrate consisting of epoxide.

* * * * *